(12) United States Patent
Pratt et al.

(10) Patent No.: US 7,846,318 B2
(45) Date of Patent: Dec. 7, 2010

(54) POLYALUMINUM CHLORIDE AND ALUMINUM CHLOROHYDRATE, PROCESSES AND COMPOSITIONS: HIGH-BASICITY AND ULTRA HIGH-BASICITY PRODUCTS

(75) Inventors: William E. Pratt, Morehead City, NC (US); Joseph J. Stevens, West Point, MS (US); Peter G. Symons, Williamsville, NY (US)

(73) Assignee: Nextchem, LLC, West Point, MO (US)

( * ) Notice: Subject to any disclaimer, the term of this patent is extended or adjusted under 35 U.S.C. 154(b) by 383 days.

(21) Appl. No.: 11/619,483

(22) Filed: Jan. 3, 2007

(65) Prior Publication Data
US 2007/0187256 A1    Aug. 16, 2007

Related U.S. Application Data

(60) Provisional application No. 60/756,848, filed on Jan. 6, 2006, provisional application No. 60/829,804, filed on Oct. 17, 2006.

(51) Int. Cl.
*C25D 5/34* (2006.01)
*C25B 1/24* (2006.01)
*B01D 61/00* (2006.01)
*C01B 17/45* (2006.01)
*C01B 17/46* (2006.01)

(52) U.S. Cl. .................. 205/208; 423/467; 205/498; 204/523

(58) Field of Classification Search .................. None
See application file for complete search history.

(56) References Cited

U.S. PATENT DOCUMENTS
2,854,382 A    9/1958    Grad
(Continued)

FOREIGN PATENT DOCUMENTS
CN    1186773    7/1998
(Continued)

OTHER PUBLICATIONS

Rosenberg, Richard; *Soap, Perfumery & Cosmetics*, (2000), vol. 7, pp. 26-28.
(Continued)

*Primary Examiner*—Melvin C Mayes
*Assistant Examiner*—Sarah Van Oudenaren
(74) *Attorney, Agent, or Firm*—Scott D. Rothenberger; Fulbright & Jaworski (57) ABSTRACT

The invention relates generally to processes for the production of high-basicity and ultra-high basicity polyaluminum chlorides including aluminum chlorohydrate. The processes can produce products of a wide range of basicities and are particularly useful in producing high basicity products. The process can produce a wide range of solution concentrations and are particularly useful in producing high solution concentrations. The processes described generate high purity products, which are free of by-product salt(s). The processes described herein can also be utilized to produce enhanced efficacy polyaluminum chlorides including aluminum chlorohydrate. When compared to conventional processes for manufacturing these compounds the processes disclosed herein are unique in so far as the disclosed processes do not require aluminum metal as a starting material. The products of the processes are suitable in applications including water purification, catalysts, and antiperspirants. In addition, the invention is directed to the products prepared by the processes described herein.

60 Claims, 5 Drawing Sheets

Electrodialysis Stack Showing the Removal of Electrolyte, MX from Depleting Solution and the Concentration of MX in the Receiving Solution

U.S. PATENT DOCUMENTS

| | | |
|---|---|---|
| 3,113,911 A | 12/1963 | Jones |
| 3,282,857 A | 11/1966 | Fitch et al. |
| 3,767,549 A | 10/1973 | Sasaki et al. |
| 4,147,605 A | 4/1979 | Schenker |
| 4,203,822 A | 5/1980 | Schenker |
| 4,331,609 A | 5/1982 | Orr |
| 4,359,456 A | 11/1982 | Gosling |
| 4,608,141 A | 8/1986 | Chlanda |
| 4,775,478 A | 10/1988 | Voss |
| 4,775,528 A | 10/1988 | Callaghan et al. |
| 4,871,525 A | 10/1989 | Giovanniello |
| 5,064,538 A | 11/1991 | Boeteng |
| 5,141,610 A | 8/1992 | Vaughan |
| 5,202,115 A | 4/1993 | Vincenti et al. |
| 5,258,109 A | 11/1993 | Vaughan |
| 5,264,097 A | 11/1993 | Vaughan |
| 5,378,400 A | 1/1995 | Parusel |
| 5,384,017 A | 1/1995 | Lumbrso |
| 5,718,876 A | 2/1998 | Parekh |
| 5,955,064 A | 9/1999 | Giovanniello |
| 5,985,234 A | 11/1999 | Dulko |
| 5,997,838 A | 12/1999 | Dulko |
| 6,036,935 A | 3/2000 | Dulko |
| 6,042,816 A | 3/2000 | Shen |
| 6,149,897 A | 11/2000 | Swaile |
| 6,245,325 B1 | 6/2001 | Shen |
| 6,451,296 B1 | 9/2002 | Li |
| 6,485,812 B1 | 11/2002 | Sekiguchi |
| 6,649,152 B2 | 11/2003 | Carrillo |
| 6,902,724 B1 | 6/2005 | Parekh |
| 6,991,780 B2 | 1/2006 | Carrillo |

FOREIGN PATENT DOCUMENTS

| | | |
|---|---|---|
| CN | 1186773 A | 7/1998 |
| DE | 2310073 | 9/1973 |
| DE | 223424 | 6/1985 |
| FR | 2384861 | 10/1978 |
| JP | 48055195 | 8/1973 |
| JP | 48060099 | 8/1973 |
| JP | 7-803 | 1/1995 |
| JP | 7-80253 | 3/1995 |
| RO | 63835 | 4/1979 |

OTHER PUBLICATIONS

Lu, Guang-jie; Zhongguo Huanjing Kexue, (2000), vol. 20(3), pp. 250-253.

Qu, Jiuhui; *Faming Zhuanli Shenqing Gongkai Shuominshu*, Derwent Abstract.

Rosenberg & Allan; *Soap, Perfumery & Cosmetics*, (1997), vol. 7, pp. 27-30.

White, D.A., *Journal of Membrane Science*, (1996), 113(2) 331-125:17950.

Krasii, B.V.; Khimiya I Tekhnologiya Topliv I Masel, (1991), (2) pp. 10-12, 115:117266.

Terada, Ichiro; Garasau Kenkyu Hokoku, (1997), 4(1/2) 59-127:222385.

Besman, V.L.; Akademiya Nauk Kazakhskoi SSR, (1975), (51), pp. 93-101, 84:10821.

Isaev, N.I.; Zhurnal Fizicheskoi Khimi, (1969), vol. 43(7), pp. 1742-1746, 71:116896.

Figure 1.
Electrodialysis Stack Showing the Removal of Electrolyte, MX from Depleting Solution
and the Concentration of MX in the Receiving Solution

FIGURE 5.
Schematic Representation of Bipolar Membranes to Increase the
Basicity of Polyvalent Metal Hydroxychlorides Bipolar Cell Configuration Employed for Production of ACH at 40°C

FIGURE 6.
Cell Configuration of Bipolar Electrodialysis Stack

POLYALUMINUM CHLORIDE AND ALUMINUM CHLOROHYDRATE, PROCESSES AND COMPOSITIONS: HIGH-BASICITY AND ULTRA HIGH-BASICITY PRODUCTS

CROSS REFERENCE TO RELATED APPLICATIONS

This application claims benefit under 35 U.S.C. §119(e) to U.S. Ser. No. 60/756,848, entitled "Process for Increasing the Basicity of Polymetal Halides", filed Jan. 6, 2006 by William E. Pratt and Joseph J. Stevens.

This application also claims benefit under 35 U.S.C. §119 (e) to U.S. Ser. No. 60/829,804, entitled "Polyaluminum chloride and Aluminum Chlorohydrate, Processes and Compositions: High-Basicity and Ultra High Basicity Products", filed Oct. 17, 2006 by William E. Pratt and Joseph J. Stevens, the contents this provisional application of which are incorporated herein by reference in their entirety.

FIELD OF THE INVENTION

This invention relates to a process to produce high basicity polyaluminum chloride and aluminum chlorohydrate by electrodialysis.

BACKGROUND OF THE INVENTION

Polyaluminum chloride (PAC) is the name given to the family of compounds defined by the formula:

$$Al_m(OH)_nCl_{3m-n}$$

Where $0<n\leq 3m$ and where $m\geq 1$. The degree of neutralization (i.e., the OH to Al ratio) is known as the basicity. In the case of polyaluminum chlorides the basicity is defined by the formula n/3m.

The solution chemistry of polyaluminum chlorides is complex. Although the formation of polynuclear aluminum species has been studied for over a century, there is still much controversy concerning aluminum polymerization reactions and the resulting product compositions. In general these materials are known to form a variety of oligomers and polymers in solution. Basicity is a major factor in determining the molecular species distribution; low-basicity favors low molecular weight species and high-basicity favors high molecular weight species. Temperature and concentration also effect the molecular species distribution but in less predictable ways.

PAC's can be broadly divided into three groups of basicities based on the manufacturing techniques used for their production. Low-basicity PAC with basicity from ~1% to ~45% is manufactured by the well known reaction of aluminum trihydrate ($Al_2O_3$—$3H_2O$) with hydrochloric acid or aluminum chloride. High-basicity PAC with basicity of ~45% to about ~65% is manufactured by two methods. The first method known as the neutralization process relies on the reaction of aluminum chloride or low-basicity PAC with a base. The second method known as the oxidation process relies on the reaction of hydrochloric acid or aluminum chloride or low-basicity PAC with aluminum metal. And ultra high-basicity PAC (including ACH) with basicity of ~65% to ~83% is manufactured by the oxidation process (i.e., the reaction of hydrochloric acid or aluminum chloride or low-basicity PAC with aluminum metal. Based on these conventional processes for manufacturing PAC, high-basicity and ultra high-basicity products cost more to manufacture than low basicity products. The higher costs related to increased basicity is due to the relatively high cost of aluminum metal in comparison to other sources of aluminum (in the oxidation process) and the costs of acids and bases wasted in the neutralization process (vide infra).

Polyaluminum chlorides are used in diverse applications including catalysts, water treatment and antiperspirants. Each of these applications relies on the neutralization of PAC to form insoluble aluminum hydroxide. Although products with basicities ranging from ~1% to ~83% have commercial utility, the products with higher basicities generally have greater utility. Thus, catalyst applications favor PAC with basicity of ~83%, antiperspirant applications favor basicities from ~65% to ~83% and water treatment applications favor PAC with basicities from ~50% to ~83%. The highest basicity PAC of commercial interest is the polyaluminum chloride with ~83% basicity known as aluminum chlorohydrate (ACH); it has an empirical formula of $Al_2(OH)_5Cl$.

The challenges of satisfying the product requirements of these applications are many. In general, high concentration (i.e., high $Al_2O_3$ content) products are preferred when compared to low concentration counterparts. Thus catalyst applications require products with an $Al_2O_3$ content of ~23.5% $Al_2O_3$. Antiperspirant applications frequently use dry products and processes which yield high $Al_2O_3$ content are desirable in order to minimize evaporation costs. In water treatment applications, PAC generally works more efficiently, produces less by-product sludge, settles faster, works better in cold water and reduces the pH of the water to a lesser extent than alternative products. In this application high-basicity PAC products with low $Al_2O_3$ content are generally favored. These product characteristics are common in water treatment because this product application can tolerate the presence of inert salts, and because this type of product can be economically manufactured by the neutralization process.

High-basicity (or ultra high-basicity) products are generally preferred in comparison to low-basicity products. And high $Al_2O_3$ content products are generally preferred in comparison to low $Al_2O_3$ content products. In many cases high-basicity (or ultra high-basicity) products with high $Al_2O_3$ content are preferred.

The reaction of aluminum chloride or hydrochloric acid with aluminum trihydrate used to manufacture low-basicity PAC has limited versatility. The reaction proceeds at elevated temperature and ambient pressure to produce products of modest basicity (<5% to 10%). Under moderate pressure, (up to 7 atm.) basicities of up to 40% to 45% are obtained. However, due to the corrosive nature of the reaction medium and the cost of operating at higher pressure, it is not practical to manufacture higher basicity products with this approach. PAC with forty-percent basicity is manufactured and sold commercially at a PAC concentration of about 36% (~17.1% $Al_2O_3$).

The commercial process used for manufacturing high-basicity PAC, involves the neutralization reaction of aluminum chloride or low-basicity PAC with base and is shown below.

$$Al_2(OH)_nCl_{6-n} + M^+Base^- \longrightarrow Al_2(OH)_{n+1}Cl_{6-(n+1)} + MCl$$

(In this reaction $M^+$ is either an alkali ion, alkali earth ion or aluminum ion.) Processes which rely on bases (e.g. alkali hydroxides and/or carbonates, or alkali earth hydroxides and/or carbonates, or sodium aluminate) to produce higher basicity PAC's suffer from several limitations. The formation of salt (i.e., MCl) from the neutralization process limits the solubility and the stability of the products formed. Procedures for separating the high-basicity PAC from the salt, MCl, are not known. Therefore this procedure is unsuitable for making pure high-basicity PAC. Moreover, this approach is wasteful of raw materials (e.g., the hydrogen chloride and the base consumed in the neutralization process). Commercial products available by this route have low $Al_2O_3$ concentrations (less than 12.5% $Al_2O_3$ concentration is typical) due to the salt present from the neutralization process and have limited stability. Low concentration products are expensive to transport to end use customers.

The waste of raw materials in the neutralization process is worthy of elaboration. The reaction of aluminum chloride with calcium carbonate is typical:

$$2AlCl_3 + 2CaCO_3 \longrightarrow Al_2(OH)_4Cl_2 + 2CaCl_2$$

Aluminum chloride is manufactured by the reaction of hydrochloric acid with aluminum trihydrate. Thus, in the neutralization reaction above, four moles of hydrochloric acid and two moles of calcium carbonate are sacrificed in order to increase the basicity to 66%. In this example 1.15 lb of calcium chloride are produced for every pound of 66% basicity PAC produced. The raw material consumed by the neutralization process is wasteful and expensive. In addition, the calcium chloride generated in this process remains with the product thereby adding to overall solution concentration, and thereby reducing the solubility and stability of the PAC. The neutralization process has limited utility for manufacturing ultra high-basicity PAC due to the amount of co-product salt generated and the waste of raw materials.

High-basicity and ultra high-basicity PACs, including ACH are generally manufactured by the oxidation of aluminum metal in the presence of aluminum chloride, low basicity PAC or hydrochloric acid, the reaction below is typical.

$$3HCl + 6 Al (metal) + 15 H_2O \longrightarrow 3 Al_2(OH)_5Cl + 9 H_2$$

This reaction yields high purity product because aluminum is readily available in high purity (99.7% and higher). This process is however not without limitations. Aluminum metal is expensive; on a contained aluminum basis, aluminum metal is two and a half to four times more expensive than the ATH used to manufacture low-basicity PAC's. The process is dangerous because hydrogen can undergo violent explosions. The reaction utilizes either, aluminum ingot, shot, or powder. Aluminum shot is more expensive than aluminum ingot, and powder is more expensive than shot. Aluminum ingot is slow to react and long batch times (up to 7 to 10 days) are common. Aluminum shot is easier to handle and somewhat more reactive (5 to 7 day reaction times are common), however the process is unpredictable; high turbidity batches requiring extensive settling and filtration are not uncommon. Aluminum powder gives faster reaction times (1 to 4 days depending on the size of the reaction), however powder requires special procedures due to its tendency to explode when exposed to air, static, or sparks.

Thus, more efficient processes are needed for manufacturing high-basicity PAC and ultra high-basicity PAC. Accordingly the present invention provides processes for manufacturing low-basicity, high-basicity and ultra high-basicity PAC products The processes of the present invention are not reliant on aluminum metal for producing ultra high-basicity products. The processes of the present invention provide highly efficient means for producing high-basicity products since the wasteful neutralization step practiced by conventional processes is eliminated.

BRIEF DESCRIPTION OF THE DRAWINGS

FIG. 3 is a schematic representation which depicts one mode of operation for the over all process. In this schematic the receiving solution and the depleting solution are both comprised of polyaluminum chloride solutions. The depleting solution becomes more basic and the receiving solution becomes less basic due to the electrodialysis process. This illustration depicts one aspect of the present invention: hydrochloric acid removed from the depleting solution and captured by the receiving solution is recycled to PAC production preventing the waste of hydrochloric acid which is common to the neutralization process practiced today.

SUMMARY OF THE INVENTION

The present invention is directed toward the production of PAC including high-basicity and ultra high-basicity PAC. The products are unique since they are produced without the use of expensive aluminum metal and without the use of bases (e.g. alkali hydroxides and/or carbonates, or alkali earth hydroxides and/or carbonates, or sodium aluminate). Products produced by the present invention are stable and are produced in various concentrations including high (>12.5%) $Al_2O_3$ concentrations.

In one aspect, the present invention provides a method to increase the hydroxide content of compounds comprising the formula (I):

$$M_m(OH)_nX_{am-n} \qquad \text{(Compound I)}$$

wherein M is a metal that undergoes the reaction:

$$M_mX_{am} \text{ (Compound II)} + H_2O \rightleftharpoons M_m(OH)_nX_{am-n} \text{ (I)} + HX$$

wherein "a" is the valence of the metal ion;
X is an anion;
$0 < n \leq am$; and
$m \geq 1$.

The process includes the step of subjecting a solution of Compound I that can hydrolyze to generate HX to electrodialysis or subjecting Compound II that can hydrolyze to form Compound I with generation of HX to electrodialysis wherein either: i. cation permeable membranes and anion permeable membranes or bipolar membranes and anion permeable membranes are utilized, and ii. enriching and depleting streams are both composed of Compounds of Formula I, such that the HX concentration is decreased from the depleting solution. The electrodialysis process provides Compound I in the depleting stream with increased hydroxide content relative to Compound I prior to the electrodialysis treatment.

In one aspect, initial Compound I and/or Compound II are freshly prepared and or subjected to heat treatment prior to or during the electrodialysis process.

In another aspect, the electrodialysis process is operated at elevated temperature of from about 30° C. to the maximum temperature allowed by electrodialysis equipment, e.g., about 65° C.

In still another aspect, the enriching solution is polyaluminum chloride.

In still another aspect, the enriching solution from the electrodialysis process is reacted with aluminum trihydrate and reused in the electrodialysis process.

In still yet another aspect, the depleting solution has a concentration of aluminum ion greater than 1 molar.

In still another aspect, the products have a basicity greater than 45% but less than 65%.

In yet another aspect of the process of the invention, the products have a basicity of greater than or equal to 65%.

In still another aspect of the process of the invention, the product is ACH with an aluminum to chloride ratio between about 1.9:1 to about 2.1:1.

In another aspect, the process of the invention provides that M is Al, Ti, Zr, or Fe.

In still yet another aspect, X is a halide, and in particular is chloride.

In yet another aspect of the invention, sulfate ion and or phosphate ion is incorporated either before, during or after the electrodialysis process and/or calcium ions or other alkali earth ions are incorporated either before, during or after the electrodialysis process.

DETAILED DESCRIPTION OF THE INVENTION

The ability of aluminum ion to hydrolyze water is one of the substance's best known characteristics. The present invention utilizes this attribute to increase the basicity of PAC's. Thus, extracting hydrochloric acid from the reaction below drives the equilibrium to the right, thereby increasing the basicity of PAC. Moreover, the present invention teaches convenient methods for removing the hydrochloric acid in a form so that it can be reused; this feature avoids the waste characteristic of the neutralization process practiced commercially for the production of high-basicity PAC.

$$Al_2(OH)_mCl_{6-m} + H_2O \rightleftharpoons Al_2(OH)_{m+1}Cl_{6-(m+1)} + HCl$$

The process of the present invention therefore provides methods for increasing the basicity of PAC's. The methods herein are highly efficient because the use of expensive aluminum metal as a raw material is avoided. The methods are also highly efficient because the wasteful neutralization of hydrochloric acid is avoided.

The process taught by the present invention can produce a variety of product concentrations, of particular interest is the process' ability to produce products with high (>12.5%) $Al_2O_3$ concentrations. Because the process of the present invention avoids the production of by-products salts, the PAC's so formed are highly stable even at high (>12.5%) $Al_2O_3$ concentrations. The products are useful in a variety of applications including water treatment, paper making, antiperspirants and catalysts. The processes taught by the present invention produce unique products with regard to their molecular species distribution and said products perform uniquely in product applications.

The present invention embraces processes for increasing the basicity of aluminum compounds. The processes are unique when compared to existing commercial processes for making the products because the use of expensive aluminum metal is avoided and wasteful neutralization with alkalis is avoided. The processes can produce products of a wide range of basicities and are particularly useful in producing high-basicity products and ultra high-basicity products. The process can produce a wide range of solution concentrations. The processes described generate high purity products. The products of the present invention are compounds of Formula I:

$$M_m(OH)_nX_{am-n} \quad (I)$$

wherein "a" is the valence of the metal ion;
X is an anion;
$0 < n \leq am$; and
$m \geq 1$.

The present invention surprisingly provides processes that increase the hydroxide content (i.e., the basicity) of compounds having the Formula I, wherein M is a metal (or combination of metals) that undergoes the reaction below. Examples of such metals include but are not limited to aluminum, zirconium, titanium and iron.

$$M_mX_{am} \text{ (II)} + H_2O \rightleftharpoons M_m(OH)_nX_{am-n} \text{ (I)} + HX$$

The increase in hydroxide content (i.e., basicity) is accomplished by subjecting an aqueous solution of Compound I to electrodialysis, such that the HX concentration in the solution is decreased. Therefore, HX is effectively removed from the solution and from Compound I, thereby providing Compound I with increased hydroxide content relative to Compound I prior to electrodialysis treatment.

Alternatively, or in combination with the electrodialysis treatment of Compound I, Compound II can be subjected to electrodialysis which causes Compound II to undergo a transformation to form Compound I with generation of HX. Again, during the electrodialysis treatment, HX is removed from solution, thereby providing Compound I with an increased hydroxide (increased basicity) content.

In particular, M can be aluminum (Al), titanium (Ti), zirconium (Zr), or iron (Fe). X can be any mono-valent ion, a halide such as chloride, bromide, iodide, or nitrate.

When M is equal to aluminum the aforementioned processes produce products with a wide range of basicities. While the processes of the present invention are capable of producing a full range of basicities, the processes preferably produce products of basicity greater than about 50%, more preferably the processes produce products of basicity greater than 60%, and most preferably the process produces products of basicity greater 65%. One particular interest is the use of these processes to produce aluminum chlorohydrate with a basicity of about 83%. (in the case of aluminum chlorohydrate, X is Cl in the above formula and the aluminum to chloride ratio is from about 1.9:1 to about 2.1:1)

Preferred aluminum salts for use as starting materials are those having the empirical formula $Al_2(OH)_nX_{6-n}$ wherein X is Cl, Br, I, or $NO_3$, preferably Cl. The processes of the present invention are applicable to materials wherein n ranges from about 0 to about 5, however materials defined by n ranging from about 0 to about 3 are of particular interest due to their availability from economical routes. The aluminum salts also generally have some water of hydration associated with them.

Calcium ions are known to stabilize polyaluminum chloride compositions. Said calcium ions may be introduced to products of the present invention by adding a variety of calcium salts. Said calcium salts include calcium hydroxide, calcium carbonate, calcium acetate, calcium citrate, calcium glycinate, calcium chloride, etc. and said calcium salts may be added in quantities from about 0 to about 2%. Said addition of calcium salts may be prior to, during or after the electrodialysis process.

Polyvalent anions including sulfate and phosphate are known to enhance the performance of polyaluminum chloride in water treatment. The ions can be incorporated into the products of the present invention either before, during, or after the process of raising the basicity.

The products of the present invention may be used or stored as an aqueous solution or they may be spray dried, vacuum dried or dried by other means to obtain compositions in solid powder form.

Electrodialysis is an electrochemical process in which ions are transported through ion permeable membranes from one solution to another under the influence of a potential gradient. The electrical charges on the ions allow them to be driven through the membranes fabricated from ion exchange polymers. Applying a voltage between two end electrodes generates the potential field required for ion transport across membranes to occur. Since the membranes used in electrodialysis have the ability to selectively transport ions having positive or negative charge and reject ions of the opposite charge, useful concentration, removal, or separation of electrolytes can be achieved by electrodialysis. Commercial applications of electrodialysis include:

The removal of salt from brackish water to generate drinking water.

The concentration of salt from seawater up to 20% salt content, as a first step toward salt manufacture.

The reduction of minerals from whey to manufacture infant formula.

And the reduction of salt from soy sauce.

Figure 1:
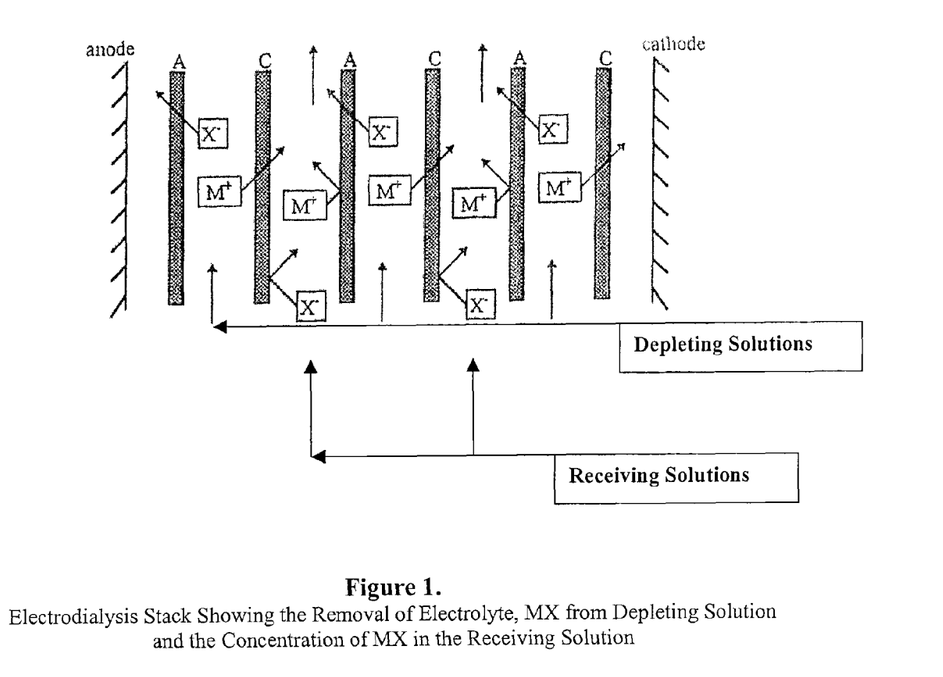
FIG. 1 depicts an electrodialysis stack and demonstrates the removal of electrolyte, MX from depleting solution and the concentration of MX in the receiving solution. The term receiving solution and enriching solution are one in the same and used interchangeably throughout this discussion.

The device used for electrodialysis processes is generally referred to as an electrodialysis stack. The essential elements of an electrodialysis stack are an anode, a cathode, cation permeable membranes and anion permeable membranes. FIG. 1 is a depiction illustrating the basic components and operation of an electrodialysis process employing monolayer membranes. Thus, the cation and anion permeable membranes are placed between the anode and the cathode in alternating fashion. Assembling the ion permeable membranes in this fashion creates two distinct sets of compartments. The first set of compartments or cells is comprised of an anion permeable membrane on the anode side and a cation ion permeable membrane on the cathode side. This set of cells is oriented with respect to the anode and the cathode so that electrolytes are depleted from these cells when a voltage is applied. The solutions in this set of compartments are referred to as the depleting stream. The second set of compartments or cells is comprised of an anion permeable membrane on the cathode side and a cation permeable membrane on the anode side. This set of cells is oriented with respect to the anode and the cathode so that electrolytes are received and concentrated in these cells when a voltage is applied to the electrodes. The solutions in this second set of compartments are referred to as the receiving or the enriching stream. Thus, the net effect of the electrodialysis process is to transfer electrolytes from the depleting solution to the receiving solution where said electrolytes are concentrated.

Successful commercial application of electrodialysis requires that the process under consideration has the ability to support a high rate of ion transfer across the ion permeable membrane surfaces for extended periods. The rate of ion transfer across membrane surfaces is referred to as the ionic flux and is measured in mole/sec-cm$^2$. The ionic flux is related to the electrical charge passed through the electrodialysis cell by the following relationship $$\text{Ionic Flux} = \frac{\text{Current Density (coulombs/sec-meter}^2\text{)}}{\text{Faraday's Constant (96,485 coulombs/mole)}}$$

Since coulombs/sec is equivalent to amperes, the current density (C.D.) is commonly measured in mamp/cm$^2$. Successful electrodialysis processes (utilizing hydrocarbon membranes configured as described above) generally support a C.D. from ~10 to ~50 mamp/cm$^2$. Current densities below ~10 mamp/cm$^2$ are generally impractical due to the large amount of ion permeable membrane required. The upper limit for current densities is generally determined by limitations of the ion permeable membranes. Monolayer hydrocarbon membranes are generally limited to ~50 mamp/cm$^2$.

Figure 2:
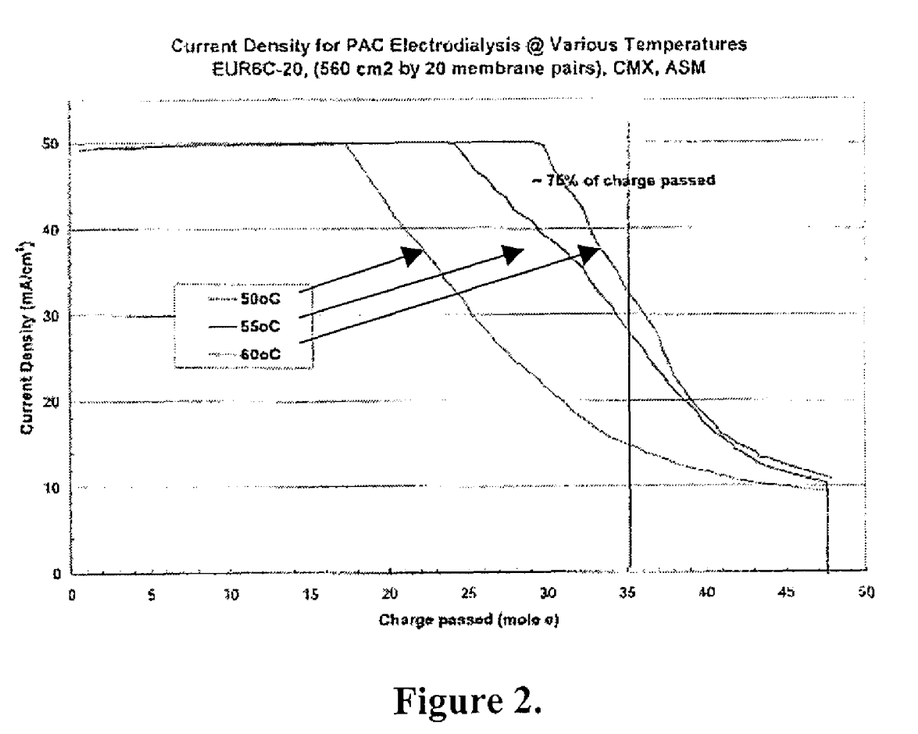
FIG. 2 shows the current density as a function of basicity at 50° C., 55° C. and 60° C. and demonstrates the benefit of operating the electrodialysis processes of the present invention at elevated temperatures.

Electrodialysis processes are commonly performed at ambient temperatures; the commercial processes mentioned above are all performed at ambient temperatures. It was surprisingly found that current densities for the processes of the present invention are markedly improved by operating at increased temperature. FIG. 2 compares the current density at 50° C., 55° C. and 60° C. as a function of basicity for the electrodialysis processes of the present invention. The information depicted in this diagram shows that current density is reduced as the basicity is increased but that the reduction in current density is mitigated by increasing temperature. This reduction in current density at increased basicity was confirmed by operating the electrodialysis processes of the present invention at various temperatures. Operation at 55° C. to 65° C. permitted current densities of 50 to 40 mamp/cm$^2$ to be realized over the range of basicities from 40% to 70%; in contradistinction operation at ambient temperature resulted in current densities of 42 to 18 mamp/cm$^2$ over the same range of basicities. At 55° C. the current density at 83% basicity was 30 mamp/cm$^2$; while operation at ambient temperature resulted in a current density of 2-4 mamp/cm$^2$ at 83% basicity. Without being bound by theory, these observations suggests that polyaluminum chlorides participate in a process that causes membrane fouling as the basicity increases and that this fouling process is mitigated as the temperature is increased.

The observations cited above demonstrate that the current density for the electrodialysis processes of the present invention increases as the temperature of operation increases. The temperature of operation for electrodialysis is limited by various characteristics related to the materials of construction of the electrodialysis stack. Although, ion permeable hydrocarbon membranes rated to 80° C. of operation are available, operation above 40° C. is uncommon. Stack distortion, spacer manufacturing technology and spacer integrity are the primary factors limiting higher temperature operation. Stack components that permit the present invention to operate at temperatures up to 65° C. were utilized in the present work. Operation at temperatures higher than 65° C., while not practical with components currently available would be beneficial to the process of the present invention.

Membrane fouling, the deposition of materials (e.g., solids and or gels) that inhibit ion permeable membrane performance, leads to membrane degradation and should be minimized in order to maintain high current densities for extended periods of time. Macromolecules with ionizable functionalities promote membrane fouling since their charge causes them to migrate to the ion permeable membrane surface but their size prevents passage through said membrane. Polyaluminum chloride solutions form macromolecules and this attribute adversely influences the performance of electrodialysis. The propensity of PAC solutions to form macromolecules increases as the basicity increases and or as the concentration of the PAC solution increases. At basicities of greater than about 50% and or concentrations above about 1 molar (measured on an aluminum basis) membrane fouling can adversely impact the processes of the present invention. It was surprisingly found that the fouling can be minimized by either using freshly prepared starting materials and or heat treating the reaction solutions prior to or during the electrodialysis process. It was surprisingly discovered, that feed stocks for the electrodialysis processes of the present invention perform best if they are less than 30 days old, preferably less than 20 days old, and most preferably used within 10 days from the time they are manufactured. The heat treating process of the present invention is conveniently performed by heating the feed solutions to a temperature of 70° C. to boiling for a period of 15 min to 24 hours. The heat treating procedure of the present invention is conveniently carried out by heating the feed solutions to a temperature of 90° C. for a period of one hour. When low-basicity PAC is subjected to the heat treating process there is a change in the molecular speciation as determined by size exclusion high pressure chromatography (HPLC). HPLC indicates that the heat treatment process induces an increase in lower molecular weight species.

Figure 4:
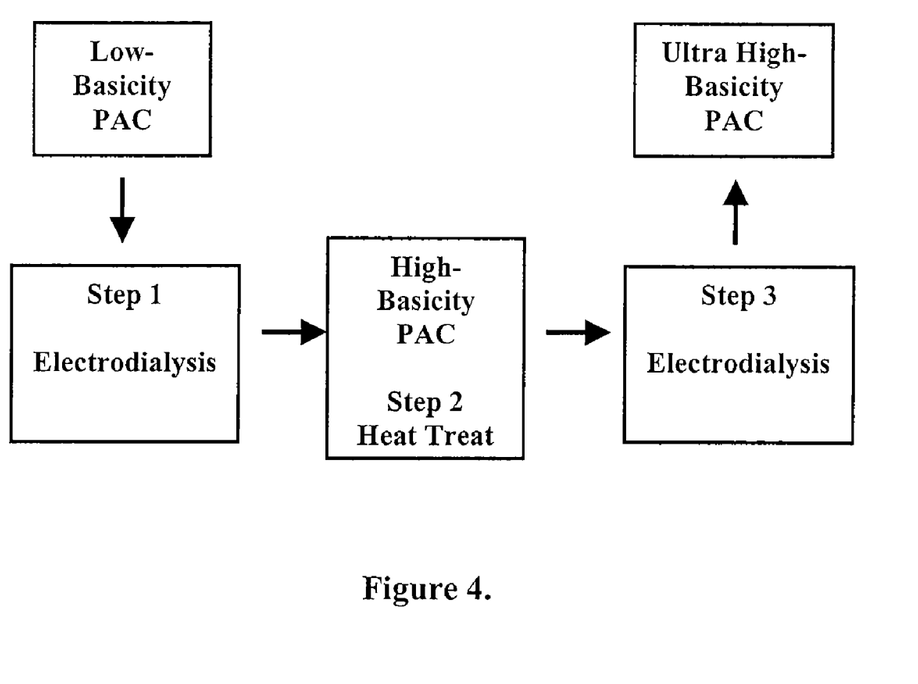
FIG. 4 is a schematic representation of the three step process for producing ultra high-basicity PAC.

The production of ultra high-basicity PAC is conveniently carried out in either a one step or a three step procedure. In the three step procedure (shown in FIG. 4) the steps are comprised of electrodialysis of low-basicity PAC (e.g. 40% PAC) to some intermediate basicity, like 65% basicity PAC to 75% basicity PAC, heat treating the product of step 1, followed by electrodialysis of the heat treated product from step 1 into the final product. It was surprisingly found that heat treating 65% to 75% PAC causes the molecular species distribution to favor high molecular weight species. In this case, the heat treating process lowers the viscosity of the intermediate PAC (i.e., 65% to 75% PAC). Lower viscosity is beneficial since, electrodialysis processes are intolerant of viscosities above ~20 cps. The three step procedure is particularly useful when ultra high-basicity PAC with $Al_2O_3$ concentrations greater than 14-17% $Al_2O_3$ is desired.

Successful application of electrodialysis also requires that the ion permeable membranes have a high degree of selectivity with respect to ion transport. Current efficiency is a measure of the selectivity of ion transport. The current efficiency is the ratio of current used by the desired process (removal of hydrogen ion and mono-valent anion (e.g., chloride) ion in the present invention) to the total current consumed by ion transport. Low current efficiencies indicate the presence of nonselective ion transport. High current efficiencies are important to the economics of electrodialysis since the current efficiency impacts the size of the electrodialysis cell, the electrical power consumed and product purity.

While back migration of anions across cation permeable membranes is uncommon, back migration of hydrogen ion across anion permeable membranes is common in acidic media. The processes of the present invention operate under acidic conditions (pH<3.5) and back migration of $H^+$ across anion membrane must be minimized in order to maintain high current efficiency. In addition, the processes of the present invention require that hydrogen ion (present in concentrations of ~$10^{-1}$ molar to ~$10^{-3}$ molar) in the depleting solution be transferred across the cation permeable membranes in preference to $Al^{+3}$ (present in concentrations of greater than 1 molar when measured on an aluminum basis). Non-selective cation transport can lead to reduced current efficiency and contamination of the receiving and or the depleting solution.

It was surprisingly discovered that highly selective ion transport (i.e., minimum back migration of $H^+$ across anion permeable membrane and minimum contamination of the depleting solution) and high current efficiencies (greater than 85%-90%) result from appropriate selection of the receiving solution employed. When polyaluminum chloride with basicity greater than ~5%, preferably basicity greater than ~10% is used as the receiving solution, the hydrochloric acid removed from the depleting solution reacts with the PAC in the receiving solution. Thus, utilizing PAC as the receiving solution maintains the hydrochloric acid concentration in the receiving solution at low levels, back migration of hydrogen ion is markedly reduced and high current efficiencies are realized.

In comparison, when PAC is replaced by aluminum chloride as the receiving solution, the solution becomes rich in hydrochloric acid and the current efficiency drops to impractical levels (<65%). The use of calcium chloride with calcium hydroxide as the receiving solution was also examined. The calcium chloride-hydroxide receiving solution gave current efficiencies of about 60% to 80%.

The overall process for the all aluminum system (i.e., when M=Al) is characterized by the reaction sequence below:

Depleting Solution:

$Al_2(OH)_{6-x}Cl_x + H_2O \longrightarrow Al_2(OH)_{6-(x-1)}Cl_{x-1} + HCl$

Figure 3:
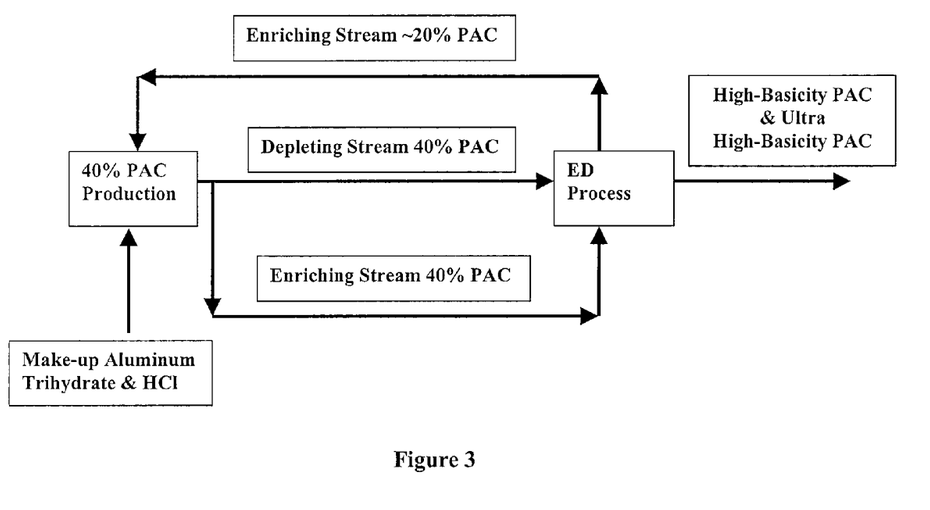

Receiving Solution:

$Al_2(OH)_{6-y}Cl_y + HCl \longrightarrow Al_2(OH)_{6-(y+1)}Cl_{y+1} + H_2O$ wherein x varies from about 2 to about 6, y varies from about 1 to about 5, and whereby the hydrochloric acid present in the PAC solution of the depleting compartments is transferred across the ion permeable membranes to the receiving solution. The hydrochloric acid so transferred across ion permeable membranes reacts with the PAC present in the receiving solution. The overall process causes the PAC in the depleting solution to become more basic (due to the current driven removal of hydrochloric acid) and the PAC in the receiving solution to become less basic. The PAC of the receiving solution is utilized in the manufacturing process as depicted in FIG. 3 wherein said PAC is removed from the electrodialysis process and its basicity is increased by reaction with aluminum trihydrate ($Al_2O_3 \cdot 3H_2O$). Thus, the overall process is highly efficient with respect to raw materials because the hydrochloric acid removed from the depleting solution is used to manufacture additional PAC (see FIG. 3).

The basicities of the PAC solutions in the reactions above and in FIG. 3 are used for illustrative purposes and other combinations of practical basicities will be readily apparent to those skilled in the art.

Most electrodialysis processes are based on the use of monolayer membranes made from functionalized organic moieties like divinylbenzene and styrene. These membranes are commonly referred to as hydrocarbon membranes in order to differentiate them from membranes made from functionalized polytetrafluoroethylenes (PTFE). The hydrocarbon membranes are inexpensive when compared to their PTFE counterparts and their use is preferred in mild applications (i.e., near neutral pH, ambient temperature, and the absence of redox processes). Hydrocarbon membranes are available as both anion permeable membranes and cation permeable membranes; while PTFE membranes are primarily available as cation permeable membranes. Interestingly, these two types of membranes have distinctly different physical structures and modes of operation. While the hydrocarbon membranes are considered to function as continuous gels, the PTFE membranes are thought to be composed of a rigid hydrophobic backbone structure filled with hydrophilic channels where ion transport takes place. While physical evidence supports the idea that hydrocarbon and PTFE membranes operate through different mechanisms, both function to provide highly effective ion transport. The processes of the present invention can be practiced with either hydrocarbon membranes or PTFE membranes.

Figure 5:
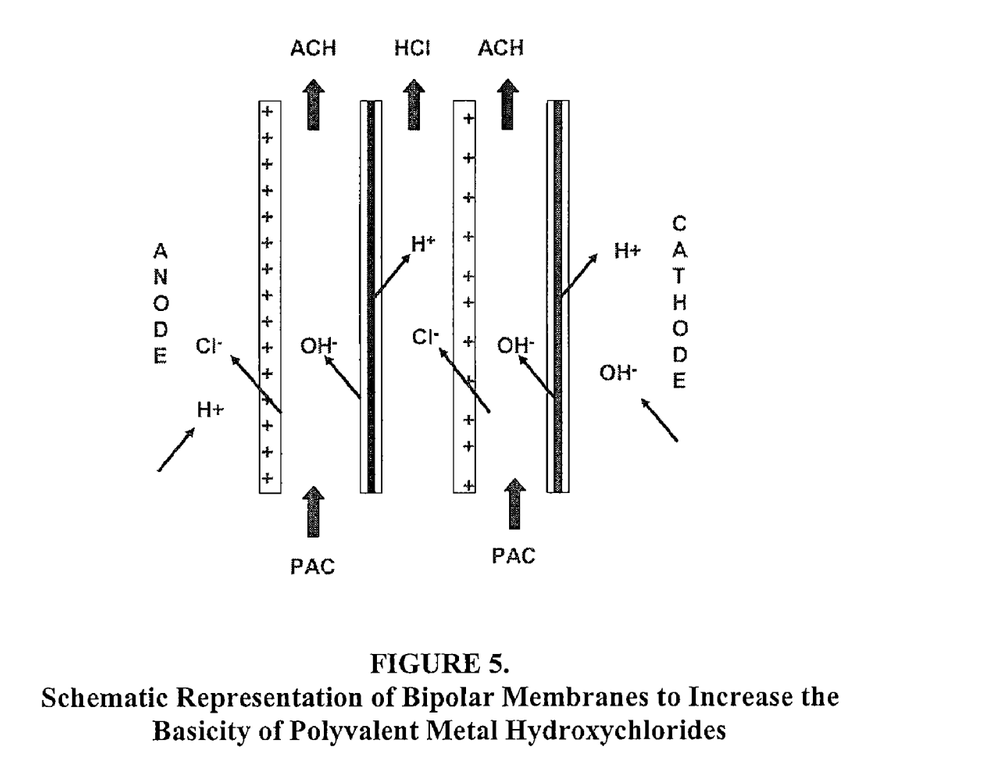
FIG. 5 is a schematic representation of an electrodialysis process where bipolar membranes are utilized to increase the basicity of a polyvalent metal.

In select applications electrodialysis processes utilize bilayer membranes commonly known as bipolar membranes. Bipolar membranes are formed by combining an anion permeable membranes and cation permeable membranes. Bipolar membranes are used in electrodialysis processes to split water. In this manner, hydrogen ions migrate through the cation ion permeable membrane toward the cathode and hydroxyl ions migrate through anion permeable membrane toward the anode. Bipolar membranes can be utilized in the process of the present invention as shown in FIG. 5.

The processes of the present invention are operated in either a batch, semi-continuous mode (commonly referred to as the "shallow dump" process) or a continuous mode (commonly referred to as the "feed and bleed" process). Shallow dump refers to a mode of operation whereby after the electrodialysis process is taken to completion, the depleting and receiving solutions are partially drained from their respective recycle loops. The recycle loops are then replenished with fresh starting solutions and the electrodialysis process is resumed. Feed and bleed refers to a mode of operation whereby the electrodialysis process is maintained in a steady state; finished product is continuously bled from the recycle loop and continuously replenished with starting material. All three modes of operation accommodate the opportunity to practice an operation known as CIP (cleaning in place) whereby the electrodialysis process is discontinued, receiving solutions and depleting solutions are removed from the electrodialysis stack and membranes are washed with a cleaning solution. Although any number of cleaning solutions may be utilized, the processes of the present invention are particularly responsive to acidic cleaning solutions; preferably hydrochloric acid cleaning solutions.

Thus, it has been found that many of the disadvantages associated with the currently known processes for manufacturing high-basicity PAC and ultra-high basicity PAC are overcome and the objects of this invention are realized by utilizing electrodialysis to increase the basicity of aluminum salts. Although the present invention can be used to produce aluminum compounds with a wide range of basicities of particular relevance is the ability to produce high-basicity and ultra-high basicity products.

In the following paragraphs, the present invention provides
paragraph 1. a method to increase the hydroxide content of compounds comprising the formula (I):

wherein M is a metal that undergoes the reaction:

wherein "a" is the valence of the metal ion;
X is an anion;
$0 < n \leq am$; and
$m \geq 1$.

The process includes the step of subjecting a solution of Compound I that can hydrolyze to generate HX to electrodialysis or subjecting Compound II that can hydrolyze to form Compound I with generation of HX to electrodialysis wherein either: i. cation permeable membranes and anion permeable membranes or bipolar membranes and anion permeable membranes are utilized, and ii. enriching and depleting streams are both composed of Compounds of Formula I, such that the HX concentration is decreased from the depleting solution. The electrodialysis process provides Compound I in the depleting stream with increased hydroxide content relative to Compound I prior to treatment.

2. The process of paragraph 1, wherein initial Compound I and/or Compound II are freshly prepared and or subjected to heat treatment prior to or during the electrodialysis process.

3. The process of paragraphs 1 or 2, wherein the electrodialysis process is operated at elevated temperature of from about 30° C. to the maximum temperature allowed by electrodialysis equipment.

4. The process of any of paragraphs 1 through 3, wherein the enriching solution is polyaluminum chloride.

5. The process of any of paragraphs 1 through 4, wherein the enriching solution from the electrodialysis process is reacted with aluminum trihydrate and reused in the electrodialysis process.

6. The process of any of paragraphs 1 through 5, wherein the depleting solution has a concentration of aluminum ion greater than 1 molar.

7. The process of any of paragraphs 1 through 6, wherein the products have a basicity greater than 45% but less than 65%.

8. The process of any of paragraphs 1 through 6, wherein the products have a basicity of greater than or equal to 65%.

9. The process of any of paragraphs 1 through 8, wherein the product is ACH with an aluminum to chloride ratio between about 1.9:1 to about 2.1:1.

10. The process of any of paragraphs 1 through 9, wherein M is Al.

11. The process of any of paragraphs 1 through 8, wherein M is Ti.

12. The process of any of paragraphs 1 through 8, wherein M is Zr.

13. The process of any of paragraphs 1 through 8, wherein M is Fe.

14. The process of any of paragraphs 1 through 13, wherein X is a halide.

15. The process of any of paragraphs 1 through 14, wherein the halide is chloride.

16. The process of any of paragraphs 1 through 15, wherein sulfate ion and or phosphate ion is incorporated either before, during or after the electrodialysis process.

17. The process of any of paragraphs 1 through 16, wherein calcium ions or other alkali earth ions are incorporated either before, during or after the electrodialysis process. While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

EXAMPLES

Except as noted in the particular examples, the experiments were carried as described in the paragraphs titled, General ED Procedure:

General ED Procedure: The ED experimental runs were carried out in a Eurodia EUR6B-15 electrodialysis stack. The stack consisted of a DSE anode and cathode and a combination of Neosepta AHA anion and Neosepta CMX cation permeable membranes. There were 15 ED membrane pairs each with an operating surface area of 0.056m². The feed (PAC) compartment consisted of a 14 liter glass reservoir and an Iwaki centrifugal circulating pump. Inlet pressure, flow, temperature, pH, and solution conductivity were monitored during the run.

The receiving loop consisted of a 14 liter glass reservoir and an Iwaki centrifugal circulating pump. The inlet pressure, pH and temperature of this solution were also monitored during the run. The electrode rinse loop consisted of a 15 liter polypropylene reservoir and an Iwaki centrifugal circulating pump. The electrode rinse solution (0.5% $H_2SO_4$) was split into two streams before entering the anode and cathode compartments. The solutions exiting the compartments were recombined in the main reservoir.

Power was supplied to the stack by two Sorensen DCS 20-50 DC power supplies connected in series. Selected data was collected during the runs (e.g., current, depleting solution and receiving solution pH, depleting solution conductivity, depleting solution and receiving solution temperature and depleting solution flow and charge passed) and several samples of each stream were taken for later analysis.

Example 1

Production of High-Basicity PAC

Electrodialysis Stack: Eurodia 6 (20 membrane pairs)
Temperature 60° C.
Membranes: Neosepta CMX and ASM
Starting Materials: 40% PAC, Holland Chemical PACL-300
Depleting: 40% PAC
Enriching Solution: $CaCl_2$
50 Liters of 40% PAC was diluted with 50 liters of deionized water. The solution was agitated and heated to 90° C. The solution was held at this temperature for 1 hour and then topped off with DI water back to a total volume of 100 L (to make up for evaporation). After cooling to 60° C., the resulting solution was fed to the electrodialysis stack as the depleting solution as described below.

The enriching solution was a 2 M $CaCl_2$ solution (10 liters). The enriching solution compartments were equipped with an apparatus that allowed for the addition of $Ca(OH)_2$ in order to maintain the pH at a value of 0.5 or greater during the course of the run. The depleting solution was also heated to and maintained at a temperature of 60° C. during the course of the run.

Circulation of the enriching and depleting solutions was begun and a potential gradient of about 14 volts was applied to the cell (~0.4 volts per membrane pair). Current was limited to 50 mA/cm². This current was maintained for 60% of the theoretical charge, when the voltage increased to the 22 V limit (0.8V/cell). This voltage was maintained for the remainder of the theoretical charge and the current dropped to 35 mA/cm² at the end of the step.

At the end of the run the depleting solution was comprised of 58 liters of 70% basic PAC & 15.4% $Al_2O_3$. Analysis for calcium showed the concentration to be about 1 g/L. The enriching solution was comprised of 49 liters of ~2 molar $CaCl_2$. The current density for the run was 46 mA/cm² and the current efficiency was 61%.

Example 2

Production of Ultra High-Basicity PAC

Electrodialysis Stack: Eurodia 6 (20 membrane pairs)
Temperature 60° C.
Membranes: Neosepta CMX and ASM
Starting Materials:
Depleting Solution: 70% PAC from Example 1
Enriching Solution: 40% PAC (diluted 1:1 with water)
58 Liters of 70% PAC (15.4% $Al_2O_3$) was diluted with 17 Liters of water; the agitated solution was heated to 90° C. The solution was held at this temperature for 1 hour and allowed to cool to 60° C. before feeding the resulting solution to the electrodialysis stack as the depleting solution as described below.

In this example the enriching solution was comprised of 23.5 Liters of 40% PAC diluted with 3 Liters of water.

Circulation of the enriching and depleting solutions was begun and a potential gradient of 22 volts was applied to the cell (0.8 volts per membrane pair). The initial current was 50 mA/cm². This voltage was maintained for the rest of the step and the current dropped to 9 mA/cm² by the end of the step.

At the end of the experiment the depleting solution was comprised of 35 liters of 82.4% basic PAC & 22.6% $Al_2O_3$. Analysis for calcium showed the concentration to be 35 ppm. The enriching solution was comprised of 60 Liters of 0.9 molar, 12% basicity PAC. The average current density for the run was 19 mA/cm² and the current efficiency was 80%.

Analysis by an independent laboratory showed the depleting solution contained high basicity product in high solution concentration and in high purity. The laboratory reported an aluminum concentration of 22.1 wt % when expressed as $Al_2O_3$ and a chloride concentration of 7.5 wt % when expressed as chloride. This corresponds to a molecular formula of $Al_2(OH)_5 0.03Cl_{0.97}$ (83.8% basicity). The calcium concentration was less than 40 ppm. Analysis for antimony, cesium, chromium, barium, bismuth, iron, lead, lithium, magnesium, manganese, molybdenum, nickel, phosphorus, potassium, silicon, sodium, sulfur, tin, titanium, vanadium,

Example 3

Production of Ultra High-Basicity PAC

Electrodialysis Stack: Eurodia 6 (15 membrane pairs)
Temperature 55° C.
Membranes: Neosepta CMX and AHA
Starting Materials:
Depleting Solution: 70.4% PAC (15.9% $Al_2O_3$)
Enriching Solution: 70.4% PAC (15.9% $Al_2O_3$)

In this example 21 liters of 70.4% (15.9% $Al_2O_3$) basicity PAC was heat treated. The heat treating procedure involved heating the agitated solution of PAC to 90° C. and maintaining that temperature for a for a period of one hour. After cooling to a temperature of 55° C., 14.7 liters of this solution was charged to the reservoir of the ED stack for the depleting solution; 6.3 liters of this solution was charged to the reservoir of the ED stack for the receiving solution. A voltage of 18 volts was applied to the electrodes as circulation of the depleting and receiving solutions was begun. The initial current density was 50 mamps/cm². The run was concluded after 22.4 moles of charge were passed. The resulting product was found to be ACH (basicity 83.1%; 21.1% $Al_2O_3$). The current efficiency was 98%.

Example 4

Production of High-Basicity PAC

Electrodialysis Stack: Eurodia 6 (15 membrane pairs)
Temperature 55° C.
Membranes: Neosepta CMX and AHA
Starting Materials:
Depleting Solution: 40% PAC
Enriching Solution: 40% PAC In this example 7.5 liters of 40% basicity PAC (17.1% $Al_2O_3$) was diluted with 6.5 liters of water and the resulting solution was heat treated. The heat treating procedure involved heating the agitated solution of PAC to 90° C. and maintaining that temperature for a for a period of one hour. After cooling to a temperature of 55° C. this solution was charged to the reservoir of the ED stack for the depleting solution. Ten liters of 40% PAC solution was charged to the reservoir of the ED stack for the receiving solution. A voltage of 18 volts was applied to the electrodes as circulation of the depleting and receiving solutions was begun. The initial current density was 50 mamps/cm². The run was concluded after 32.4 moles of charge was passed. The resulting product was found to be PAC (basicity 70%). The current efficiency was 89.2%

Example 5

Production of Ultra High-Basicity PAC

Electrodialysis Stack: Eurodia 6 (15 membrane pairs)
Temperature 55° C.
Membranes: Neosepta CMX and AHA
Starting Materials:
Depleting Solution: 40% PAC (15.9% $Al_2O_3$)
Enriching Solution: 40% PAC (15.9% $Al_2O_3$)

In this example 7.5 liters of 40% basicity PAC was diluted with 6.5 liters of water and the resulting solution was heat treated. The heat treating procedure involved heating the agitated solution of PAC to 90° C. and maintaining that temperature for a for a period of one hour. After cooling to a temperature of 55° C. this solution was charged to the reservoir of the ED stack for the depleting solution. Eight liters of 40% PAC solution was charged to the reservoir of the ED stack for the receiving solution. A voltage of 18 volts was applied to the electrodes as circulation of the depleting and receiving solutions was begun. In this experiment the initial current was limited in order to limit the initial current density to 40 mamps/cm². The run was concluded after 44.8 moles of charge was passed. The resulting product was found to be PAC (basicity 80.4%). The current efficiency was 87%.

Example 6

Production of Ultra High-Basicity PAC

Electrodialysis Stack: Eurodia 6 (15 membrane pairs)
Temperature 65° C.
Membranes: Neosepta CMX and AHA
Starting Materials:
Depleting Solution: 40% PAC
Enriching Solution: 40% PAC Heat Treatment of the Depleting Solution: 5 Liters of 40% PAC (~17.1% $Al_2O_3$) was diluted with 4.3 Liters of water; the agitated solution was heated to 90° C. The solution was held at this temperature for 1 hour and allowed to cool to 65° C. before feeding the resulting solution to the electrodialysis stack as the depleting solution as described below.

Heat Treatment of the Receiving Solution: 6.7 Liters of 40% PAC were heated to 90° C. The solution was held at this temperature for 1 hour and allowed to cool to 65° C. before feeding the resulting solution to the electrodialysis stack as the depleting solution as described below.

The depleting loop of the ED stack was charged with 9.3 Liters of the depleting solution prepared as described above. The receiving loop of the ED stack was charged with 6.7 Liters of the receiving solution prepared as described above. Circulation of the enriching and depleting solutions was begun and a potential gradient of ~16 volts was applied to the cell (0.8 volts per membrane pair). The initial current was 40 mA/cm². The current density was maintained at 40 mA/cm² and the basicity was increased to 64%. The voltage had increased to 17.99 volts at this point.

7.44 Liters of the depleting solution prepared similarly to that described above was added to the depleting loop. 4 Liters of the receiving solution prepared similarly to that described above was added to the receiving loop and the current flow was maintained. The addition of fresh solutions caused the voltage to drop and the current density returned to the level of 40 mA/cm². When the basicity of the depleting solution reached ~74% the CD was 36 mA/cm². The run was terminated at 78% basicity and the CD at this time was 34 mA/cm². 61.9 moles of charge were passed during the experiment and the current efficiency was 82%.

Example 7

Production High-Basicity PAC with Bipolar Electrodialysis

Electrodialysis Stack: ESC ED-1 (5 membrane pairs)
Temperature 40° C.
Membranes: Neosepta Bipolar BP-1 and AMX
Starting Materials:
Depleting Solution: Aluminum Chloride (10.7% $Al_2O_3$)
Enriching Solution: Potassium Chloride (2.7 molar)

and zinc were all less than 80 ppm confirming that the process produced high purity material.

Figure 6:
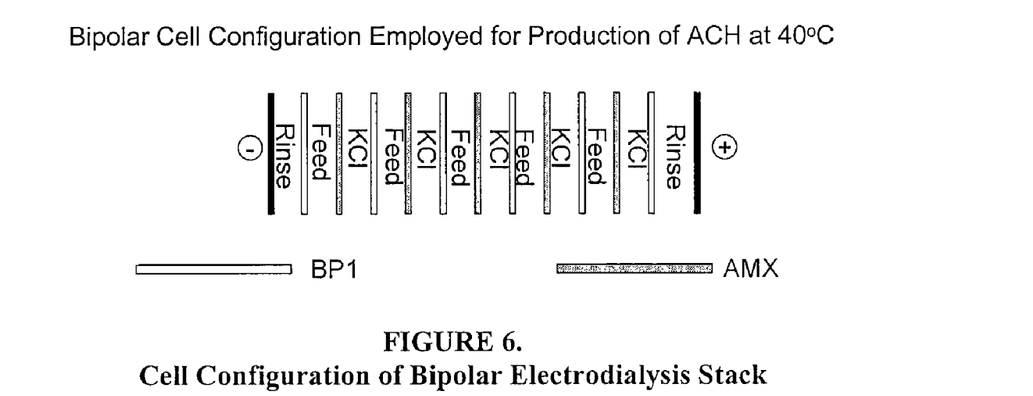
FIG. 6 is the cell configuration for a bipolar electrodialysis stack.

The ED experimental runs were carried out in an ESC ED-1 electrodialysis stack. The stack consisted of a platinized titanium anode, a 316 stainless steel cathode and a combination of Neosepta AMX anion permeable membrane and BP-1 bipolar membrane as shown in FIG. 6. The gaskets (1/32 inch) were made of EPDM and the spacers were made of polypropylene. There were 5 ED membrane pairs each with an operating surface area of 0.01 m$^2$. The feed (depleting) compartment consisted of a 1 liter glass reservoir and an Iwaki centrifugal circulating pump. Inlet pressure, flow, temperature, pH, and solution conductivity were monitored during the run.

The receiving loop consisted of a 2 liter glass reservoir and an Iwaki centrifugal circulating pump. The inlet pressure, pH and temperature of this solution were also monitored during the run. Potassium chloride solution (2.7 M) was used as the starting solution in the receiving stream. For the sake of simplicity, potassium hydroxide was added continuously to the potassium chloride solution in order to maintain the pH at a value greater than or equal to 1 during the experiment. The addition of potassium hydroxide neutralized the hydrochloric acid as it was transported across the membranes into the enrichment stream. Power was supplied to the stack by a Hewlett Packard 6010A DC power supply.

1 L of as supplied aluminum chloride 10.7% $Al_2O_3$ was used as the depleting solution. This solution was charged to the depleting loop of the electrodialysis stack. Potassium chloride (2.7 molar, 3.9 L) was charged to the receiving loop of the electrodialysis stack. Circulation of these solutions through the stack was initiated and the voltage was limited in order to maintain that current density at less than 50 mA/cm$^2$. Even though aluminum chloride has a higher nominal concentration of chloride than PAC, it should be ion paired at low basicity, as the current was initially limited. The current increased during the first 3 hours until about 30% basicity material and then the voltage started to decrease when the material reached 40% basicity. The experiment was concluded when a basicity of about 50% was obtained. Analysis of the PAC solution indicated the electrodialysis treatment produced 890 ml of PAC with an $Al_2O_3$ concentration of 12.0% and basicity 47%. This experiment demonstrated that bipolar electrodialysis is a viable route for producing high-basicity PAC.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claim.

We claim:

1. A method to increase the hydroxide content of compounds comprising the formula (I):

(Compound I)

wherein M is a metal that undergoes the reaction:

wherein "a" is the valence of the metal ion;
X is an anion;
$0 < n \leq am$;
$m \geq 1$;

comprising the step of subjecting a solution of Compound I to electrodialysis conditions to generate HX, such that the hydroxide content of Compound I is increased relative to the initial hydroxide content of Compound I, provided that
  i. cation permeable membranes and anion permeable membranes or bipolar membranes and anion permeable membranes are utilized, and
  ii. enriching and depleting streams both comprise a Compound of formula (I), such that the HX concentration is decreased from the depleting solution, thereby providing Compound I in the depleting stream with increased hydroxide content relative to Compound I prior to treatment.

2. The method of claim 1, wherein initial Compound I is freshly prepared and or subjected to heat treatment at a temperature greater than 65° C. prior to or during the electrodialysis process.

3. The method of claim 1, wherein the enriching solution comprises polyaluminum chloride.

4. The method of claim 1, wherein the products have a basicity greater than 50% but less than 65%.

5. The method of claim 1, wherein the products have a basicity of greater than or equal to 65%.

6. The method of claim 1, wherein the product is ACH with an aluminum to chloride ratio between about 1.9:1 to about 2.1:1.

7. The method of claim 1, wherein M is Al.

8. The method of claim 1, wherein M is Ti.

9. The method of claim 1, wherein M is Zr.

10. The method of claim 1, wherein M is Fe.

11. The method of claim 1, wherein X is a halide.

12. The method of claim 11, wherein the halide is chloride.

13. The method of claim 1, wherein sulfate ion and or phosphate ion is incorporated either before, during or after the electrodialysis process.

14. The method of claim 1, wherein calcium ions or other alkali earth ions are incorporated either before, during or after the electrodialysis process.

15. The method of claim 1, wherein the enriching stream has a basicity of greater than 10%.

16. A method to increase the hydroxide content of compounds comprising the formula (I):

(Compound I)

wherein M is a metal that undergoes the reaction:

wherein "a" is the valence of the metal ion;
X is an anion;
$0 < n \leq am$;
$m \geq 1$;

comprising the step of subjecting a solution of Compound I to electrodialysis conditions to generate HX, such that the hydroxide content of Compound I is increased relative to the initial hydroxide content of Compound I, provided that
  i. cation permeable membranes and anion permeable membranes or bipolar membranes and anion permeable membranes are utilized;
  ii. enriching and depleting streams both comprise a Compound of formula (I), such that the HX concentration is decreased from the depleting solution, thereby providing Compound I in the depleting stream with increased hydroxide content relative to Compound I prior to treatment; and iii. wherein the process utilizes an enriching stream comprising a Compound I with a basicity of greater than 5%.

17. A method to increase the hydroxide content of compounds comprising the formula (I):

(Compound I)

wherein M is a metal that undergoes the reaction:

wherein "a" is the valence of the metal ion;
X is an anion;
$0 < n \leq am$;
$m \geq 1$;
   comprising the step of subjecting a solution of Compound I to electrodialysis conditions to generate HX, such that the hydroxide content of Compound I is increased relative to the initial hydroxide content of Compound I, provided that
    i. cation permeable membranes and anion permeable membranes or bipolar membranes and anion permeable membranes are utilized;
    ii. enriching and depleting streams both comprise a Compound of formula (I), such that the HX concentration is decreased from the depleting solution, thereby providing Compound I in the depleting stream with increased hydroxide content relative to Compound I prior to treatment; and
    iii. wherein the pH of the enriching stream is less than a pH of 2.

18. A method to increase the hydroxide content of compounds comprising the formula (I):

(Compound I)

wherein M is a metal that undergoes the reaction:

wherein "a" is the valence of the metal ion;
X is an anion;
$0 < n \leq am$;
$m \geq 1$;
   comprising the step of subjecting a solution of Compound I to electrodialysis conditions to generate HX or subjecting Compound II to electrodialysis, wherein Compound II subsequently hydrolyzes to form final Compound I with generation of HX, such that the hydroxide content of Compound I is increased relative to the initial hydroxide content of Compound I, provided that:
    i. cation permeable membranes and anion permeable membranes or bipolar membranes and anion permeable membranes are utilized, and
    ii. enriching and depleting streams both comprise a Compound of formula (I), such that the HX concentration is decreased from the depleting solution, thereby providing Compound I in the depleting stream with increased hydroxide content relative to Compound I prior to treatment;
    iii. wherein the process utilizes an enriching stream comprising a Compound I with basicity greater than 5%; and
    iv. wherein the enriching solution from the electrodialysis process is reacted with aluminum trihydrate and reused in the electrodialysis process.

19. The method of claim 16, wherein initial Compound I is freshly prepared and or subjected to heat treatment at a temperature greater than 65° C. prior to or during the electrodialysis process.

20. The method of claim 16, wherein the enriching solution comprises polyaluminum chloride.

21. The method of claim 16, wherein the products have a basicity greater than 50% but less than 65%.

22. The method of claim 16, wherein the products have a basicity of greater than or equal to 65%.

23. The method of claim 16, wherein the product is ACH with an aluminum to chloride ratio between about 1.9:1 to about 2.1:1.

24. The method of claim 16, wherein M is Al.

25. The method of claim 16, wherein M is Ti.

26. The method of claim 16, wherein M is Zr.

27. The method of claim 16, wherein M is Fe.

28. The method of claim 16, wherein X is a halide.

29. The method of claim 28, wherein the halide is chloride.

30. The method of claim 16, wherein sulfate ion and or phosphate ion is incorporated either before, during or after the electrodialysis process.

31. The method of claim 16, wherein calcium ions or other alkali earth ions are incorporated either before, during or after the electrodialysis process.

32. The method of claim 16, wherein the enriching stream has a basicity of greater than 10%.

33. The method of claim 17, wherein initial Compound I is freshly prepared and or subjected to heat treatment at a temperature greater than 65° C. prior to or during the electrodialysis process.

34. The method of claim 17, wherein the enriching solution comprises polyaluminum chloride.

35. The method of claim 17, wherein the products have a basicity greater than 50% but less than 65%.

36. The method of claim 17, wherein the products have a basicity of greater than or equal to 65%.

37. The method of claim 17, wherein the product is ACH with an aluminum to chloride ratio between about 1.9:1 to about 2.1:1.

38. The method of claim 17, wherein M is Al.

39. The method of claim 17, wherein M is Ti.

40. The method of claim 17, wherein M is Zr.

41. The method of claim 17, wherein M is Fe.

42. The method of claim 17, wherein X is a halide.

43. The method of claim 42, wherein the halide is chloride.

44. The method of claim 17, wherein sulfate ion and or phosphate ion is incorporated either before, during or after the electrodialysis process.

45. The method of claim 17, wherein calcium ions or other alkali earth ions are incorporated either before, during or after the electrodialysis process.

46. The method of claim 17, wherein the enriching stream has a basicity of greater than 10%.

47. The method of claim 18, wherein initial Compound I is freshly prepared and or subjected to heat treatment at a temperature greater than 65° C. prior to or during the electrodialysis process.

48. The method of claim 18, wherein the enriching solution comprises polyaluminum chloride.

49. The method of claim 18, wherein the products have a basicity greater than 50% but less than 65%.

50. The method of claim 18, wherein the products have a basicity of greater than or equal to 65%.

51. The method of claim 18, wherein the product is ACH with an aluminum to chloride ratio between about 1.9:1 to about 2.1:1.

52. The method of claim 18, wherein M is Al.

53. The method of claim 18, wherein M is Ti.

54. The method of claim 18, wherein M is Zr.

55. The method of claim 18, wherein M is Fe.

56. The method of claim 18, wherein X is a halide.

57. The method of claim 56, wherein the halide is chloride.

58. The method of claim 18, wherein sulfate ion and or phosphate ion is incorporated either before, during or after the electrodialysis process.

59. The method of claim 18, wherein calcium ions or other alkali earth ions are incorporated either before, during or after the electrodialysis process.

60. The method of claim 18, wherein the enriching stream has a basicity of greater than 10%.

* * * * *